United States Patent

Lennox et al.

Patent Number: 6,096,770
Date of Patent: Aug. 1, 2000

[54] ANTHRANILIC ACID ANALOGS

[75] Inventors: Joseph Richard Lennox, Morrisville, N.C.; Schuyler Adam Antane, Lawrenceville; John Anthony Butera, Clarksburg, both of N.J.

[73] Assignee: American Home Products Corporation, Madison, N.J.

[21] Appl. No.: 09/128,492

[22] Filed: Aug. 3, 1998

Related U.S. Application Data

[60] Provisional application No. 60/054,814, Aug. 5, 1997.

[51] Int. Cl.[7] .......................... A01N 43/76; A01N 43/80; A61K 31/42; A61K 31/195

[52] U.S. Cl. .................. 514/374; 514/378; 514/563; 548/236; 548/248; 560/104; 562/495

[58] Field of Search ..................... 548/236, 248; 560/107; 592/495; 514/374, 378, 563

[56] References Cited

FOREIGN PATENT DOCUMENTS

| 0524781 | 7/1992 | European Pat. Off. . |
| WO9422807 | 10/1994 | WIPO . |

OTHER PUBLICATIONS

Derwent Abst. J5 9070654 (Lederle Japan Ltd.) (1984).

*Primary Examiner*—Johann Richter
*Assistant Examiner*—Brian J. Davis
*Attorney, Agent, or Firm*—Rebecca R. Barrett

[57] ABSTRACT

Compounds of the formula:

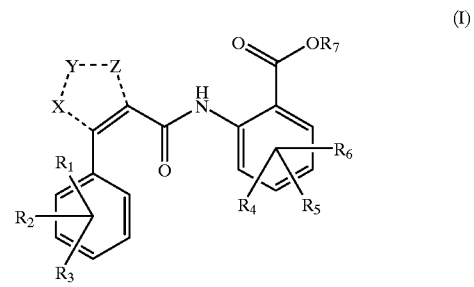

wherein:

$R_1$, $R_2$ and $R_3$ are, independently, hydrogen, nitro, cyano, $C_{1-10}$ haloalkoxy, amino, $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl and $C_{6-12}$ aryl; with the provisos: (1) that $R_1$, $R_2$ and $R_3$ may not all simultaneously be hydrogen, and (2) when $R_1$ and $R_2$ are hydrogen, $R_3$ may not be meta-$CF_3$;

$R_4$, $R_5$ and $R_6$ are, independently, hydrogen, halogen, nitro, cyano, $C_{1-10}$ carboalkoxy, $C_{1-10}$ haloalkoxy, amino $C_{1-10}$ alkylamino, sulfo, sulfamoyl, $C_{1-10}$ alkylsulfonamido, $C_{2-10}$ alkylcarboxamido, $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl, $C_{1-10}$ alkyl and $C_{6-12}$ aryl;

$R_7$ is hydrogen, metal cation, acetylamido, alkoxyacetoyl or a related moiety which delivers the carboxylate in vivo; and X, Y and Z may form a $C_{3-13}$ carbocyclic ring, oxazole, isoxazole, thiazole, isothiazole, furan, thiophene, 2H-pyrrole, pyrrole, 2-pyrroline, 3-pyrroline, imidazole, pyrazole, 1,2,3-oxadiazole or 1,2,3-triazole bound to the carbon skeleton; or pharmaceutically acceptable salts thereof useful in the treatment of disorders associated with smooth muscle contraction via potassium channel and chloride channel modulation.

12 Claims, No Drawings

ANTHRANILIC ACID ANALOGS

BACKGROUND OF INVENTION

This application claims the benefit of U.S. Provisional Application No. 60/054,814, filed Aug. 5, 1997.

The present invention relates to a novel series of anthranilic acid-derived amides (I) having pharmacological activity, to a process for their preparation, to pharmaceutical compositions containing them, and to their use in the treatment of disorders associated with smooth muscle contraction, via potassium channel and chloride channel modulation. Such disorders include, but are not limited to: urinary incontinence, asthma, premature labor, irritable bowel syndrome, congestive heart failure, angina, and cerebral vascular disease.

Modulation of potassium channels remains at the forefront of current approaches for controlling resting cell membrane potential and affecting cell excitability. A wide variety of discrete potassium channels exist and these have been thoroughly classified according to structure, function, pharmacological properties, and gating mechanisms in several recent reviews [Rudy, B. *Neuroscience* 1988, 25, 729–749; Atwal, K., *Medicinal Research Reviews* 1992, 12, 569–591; Gopalakrishnan, M. et al., *Drug Development Research* 1993, 28, 95–127; Primeau, J. et al. *Current Pharmaceutical Design* 1995, 1, 391–406; Edwards, G. et al. *Exp. Opin. Invest. Drugs* 1996, 5 (11), 1453–1464]. Therapeutic potential for potassium channel modulators in cardiovascular disorders, metabolic disorders, central nervous system disorders, bronchial asthma, and irritable bladder is being vastly explored.

Research interests in the modulation of chloride channels are growing at a fast pace [Strange, K. et al. *Kidney International* 1995, 48, 994–1003; Franciolini, F. et al. *Biochimica et Biophysica Acta* 1990, 247]. Various disease states potentially amenable to chloride channel modulation include bronchial asthma, cardiac arrhythmias, cystic fibrosis, and kidney disease.

Harita et al. disclose a process for the manufacturing of a class of meta-substituted aromatic amide carboxylic acid derivatives in Japanese Patent Application No. 49-102692, and also builds on a method for manufacturing aromatic cinammic acid derivatives in Japanese Patent Application No. 49-42465. Several patents and patent applications focus particularly on agents possessing claims of anti-allergic/anti-asthmatic/anti-histaminic activity: Sato et al. report a group of anthranilic acid derivatives (highlighting Tranilast® as an anti-allergic-agent) in Japanese Patent Application No. 57-179976; related to these anthranilates is a claim by Aoyanagi et. al. in Japanese Patent Application No. 58-79436 which discloses a method for manufacturing anthranilic acid derivatives; also related is Hungarian Patent HU 200 996 B which emphasizes the production of several Tranilast® analogs; and Yukihiko, in Japanese Patent No. J6 0019-754-A, has also indicated a method for the preparation of anthranilic acid derivatives where the styrenyl portion is strictly limited to alkoxy, hydroxy or acyloxy.

In addition, Japanese Patent No. J0 2218-654-A by Tsumoro et al. which reveals a class of amino-benzoic acid derivatives which are useful as reverse transcriptase inhibitors. Also by Tsumoro et al., Patent No. J6 0097-946-A discloses a series of substituted carboxamide derivatives which exhibit activity as leucotriene antagonists and phospholipase inhibitors.

DESCRIPTION OF THE INVENTION

In accordance with the present invention, there is provided compounds represented by the formula:

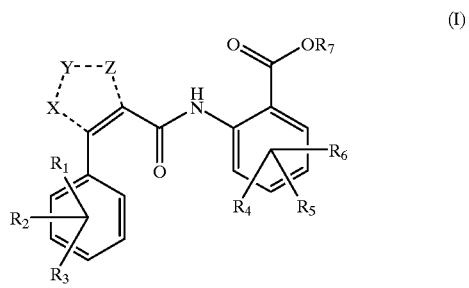

(I)

wherein:

$R_1$, $R_2$ and $R_3$ are, independently, hydrogen, nitro, cyano, $C_{1-10}$ haloalkoxy, amino, $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl and $C_{6-12}$ aryl; with the provisos: (1) that $R_1$, $R_2$ and $R_3$ may not all simultaneously be hydrogen, and (2) when $R_1$ and $R_2$ are hydrogen, $R_3$ may not be meta-$CF_3$;

$R_4$, $R_5$ and $R_6$ are, independently, hydrogen, halogen, nitro, cyano, $C_{1-10}$ carboalkoxy, $C_{1-10}$ haloalkoxy, amino $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl, $C_{1-10}$ alkyl and $C_{6-12}$ aryl;

$R_7$ is hydrogen, metal cation, acetylamido, alkoxyacetoyl or a related moiety which delivers the carboxylate in vivo;

X, Y and Z may form a $C_{3-13}$ carbocyclic ring, oxazole, isoxazole, thiazole, isothiazole, furan, thiophene, 2H-pyrrole, pyrrole, 2-pyrroline, 3-pyrroline, imidazole, pyrazole, 1,2,3-oxadiazole or 1,2,3-triazole bound to the carbon skeleton.

In more preferred aspects of the invention are included compounds of formula (I) wherein:

$R_1$, $R_2$ and $R_3$ are, independently, hydrogen, nitro, cyano, perhaloalkoxy, amino, $C_{1-10}$ alkylamino, $C_{1-10}$ dialkylamino, $C_{6-12}$ arylamino, $C_{1-10}$ aralkylamino, sulfo, sulfamyl, $C_{1-10}$ alkylsulfonamido, $C_{6-12}$ arylsulfonamido, $C_{2-10}$ alkylcarboxamido, $C_{6-12}$ arylcarboxamido, $C_{2-10}$ alkanoyl, $C_{6-12}$ aryloxyl, $C_{2-22}$ aralkanoyl, $C_{1-10}$ alkylsulfonyl, $C_{1-10}$ perhalosulfonyl, $C_{6-12}$ arylsulfonyl, $C_{2-22}$ aralkylsulfonyl, $C_{1-10}$ carboxyl, $C_{1-10}$ haloalkyl, $C_{1-10}$ perhaloalkyl, aryl, haloaryl, perhaloaryl, $C_{1-10}$ aralkyl moiety; with the provisos: (1) that $R_1$, $R_2$ and $R_3$ may not all simultaneously be hydrogen, and (2) when $R_1$ and $R_2$ are hydrogen, $R_3$ may not be meta-$CF_3$;

$R_4$, $R_5$, and $R_6$, are, independent of each other, hydrogen, halogen, nitro, cyano, carboalkoxy, perhaloalkoxy, amino, $C_{1-10}$ alkylamino, $C_{1-10}$ dialkylamino, arylamino, $C_{1-10}$ aralkylamino, sulfo, sulfamyl, $C_{1-10}$ alkylsulfonamido, $C_{6-12}$ arylsulfonamido, $C_{2-10}$ alkylcarboxamido, $C_{6-12}$ arylcarboxamido, $C_{2-10}$ alkanoyl, $C_{6-12}$ aryloyl, $C_{2-22}$ aralkanoyl, $C_{1-10}$ alkylsulfonyl, $C_{1-10}$ perhalosulfonyl, $C_{6-12}$ arylsulfonyl, $C_{2-22}$ aralkylsulfonyl, $C_{1-10}$ carboxyl, $C_{1-10}$ straight chain alkyl, $C_{1-10}$ branched alkyl, $C_{3-10}$ cyclic or bicyclic alkyl, $C_{1-10}$ haloalkyl, $C_{1-10}$ perhaloalkyl, $C_{2-1}$ alkenyl (single or multiple olefinic), aryl, haloaryl, perhaloaryl, $C_{1-10}$ aralkyl;

$R_7$ is a hydrogen, an alkali metal cation, an alkaline earth metal cation, acetylamido, alkoxyacetoyl, or related moieties which deliver the carboxylate in vivo; and X, Y and Z may form a $C_{3-13}$ carbocyclic ring, oxazole, isoxazole, thiazole, or isothiazole, bound to the carbon skeleton.

Still more preferred aspects of this invention includes compounds of formula (I) wherein:

$R_1$, $R_2$, $R_3$, $R_4$, $R_5$, and $R_6$ are as hereinbefore defined;

$R_7$ is selected from the group consisting of hydrogen, a metal cation, a moiety selected from:

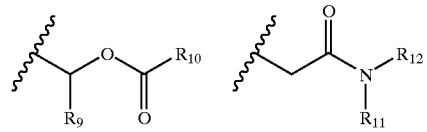

wherein:

$R_9$, $R_{10}$, $R_{11}$ and $R_{12}$, are, independent of each other, hydrogen, $C_{1-10}$ straight chain alkyl, $C_{1-10}$ branched alkyl, $C_{3-10}$ cyclic or bicyclic, aryl, or $C_{1-10}$ aralkyl; and X, Y and Z may form a $C_{3-13}$ carbocyclic ring, oxazole, isoxazole, thiazole, or isothiazole, bound to the carbon skeleton;

A most preferred aspect of this invention includes compounds of the formula (I) wherein $R_7$ may be hydrogen, or a metal cation as previously described.

It is understood that the definition of the compounds of formula (I) when $R_1$, $R_2$, $R_3$, $R_4$, $R_5$, $R_6$, $R_7$, or the ring system formed by X, Y and Z contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques or enantiomer specific synthesis. It is understood that this invention encompasses all crystalline forms of compounds of formula (I). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where $R_1$, $R_2$, $R_3$, $R_4$, $R_5$, $R_6$, or the ring system formed by X, Y and Z contains a carboxyl group, salts of the compounds in this invention may be formed with bases such as alkali metals (Na, K, Li) or alkaline earth metals (Ca or Mg).

The present invention also provides a process for the preparation of compounds of the formula (I). Methods of preparation are shown in Schemes 1 through 4.

Isoxazoles of the formula (I) may be prepared (Scheme 1) by nitrile oxide cycloaddition of a compound of the formula (II) with an appropriate nitrile oxide (III) to give heterocyclic (IV). As above, saponification gives intermediate carboxylic acid (V)

Scheme 1

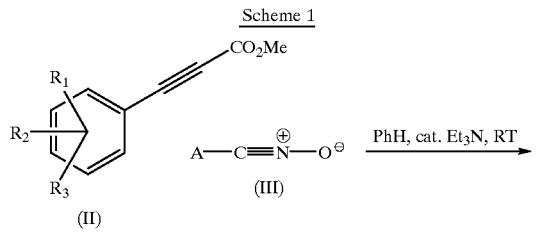

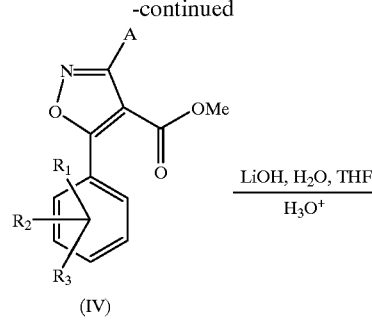

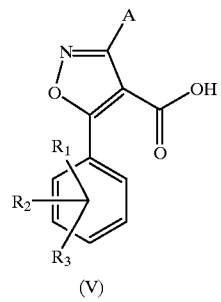

where $R_1$, $R_2$ and $R_3$ are equivalent to the aforementioned $R_1$, $R_2$, and $R_3$, and where A may be optionally selected from the groups $R_1$, $R_2$, $R_3$, $R_4$, $R_5$, $R_6$ or $R_7$.

Oxazoles of the formula (I) may be prepared (Scheme 2) via condensation of the appropriate benzoyl chloride (VI) with methyl isocyanoacetate (VII) to give the heterocycle (VIII). As above, saponification affords the intermediate carboxylic acid (IV).

Scheme 2

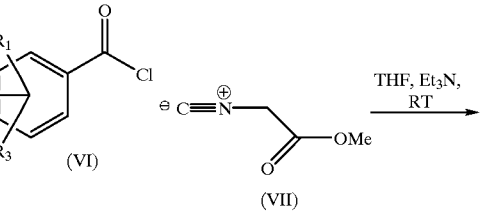

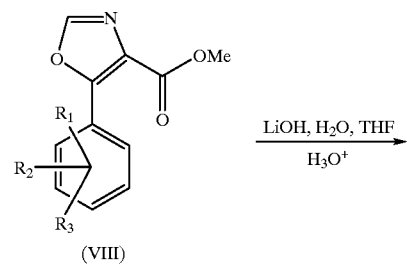

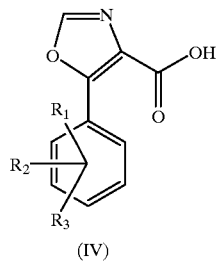

where $R_1$, $R_2$ and $R_3$ are equivalent to the aforementioned $R_1$, $R_2$, and $R_3$.

In a more general sense, compounds of the formula (I) may also be prepared (Scheme 3) by reaction of an appropriately activated hetero or carbocyclic olefin of the formula (IX) with a suitable coupling partner of the formula (X) to afford a series of compounds of formula (XI) where typical examples of the activated intermediates have M as O-trifluoromethanesulfonate, and M' as a trialkylstannane, or alternatively M as bromide or iodide with M' as a boronic acid.

Scheme 3

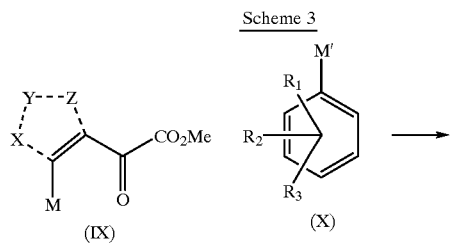

(IX)   (X)

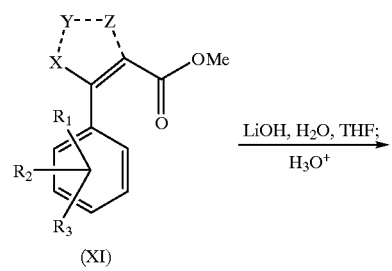

(XI)

LiOH, H₂O, THF;
H₃O⁺

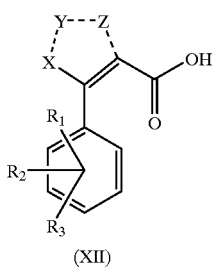

(XII)

where X, Y, Z, $R_1$, $R_2$ and $R_3$ are equivalent to the aforementioned X, Y, Z, $R_1$, $R_2$, and $R_3$. As above, saponification will lead to intermediate carboxylic acid (XII).

Carboxylic acid intermediates (V), (VI), or (XII) could subsequently be coupled (Scheme 4) to the amine of an appropriately derivatives anthranilic acid of the formula (XIII) utilizing one of the following established coupling procedures (Method A: (COCl)₂, cat. DMF, CH₂Cl₂, then add the neat acid chloride to a solution of anthranilic acid in sodium hydroxide; Method B: diisopropylcarbodiimide, DMAP, CH₂Cl₂, then add methyl anthranilate; or Method C: (COCl)₂, cat. DMF, CH₂Cl₂, or SOCl₂ followed by treatment of the neat acid chloride with triethylamine and methyl anthranilate) to afford amides of formula (I). if the esters of (XIII) are used, then final saponification affords the free acids (R₇=H).

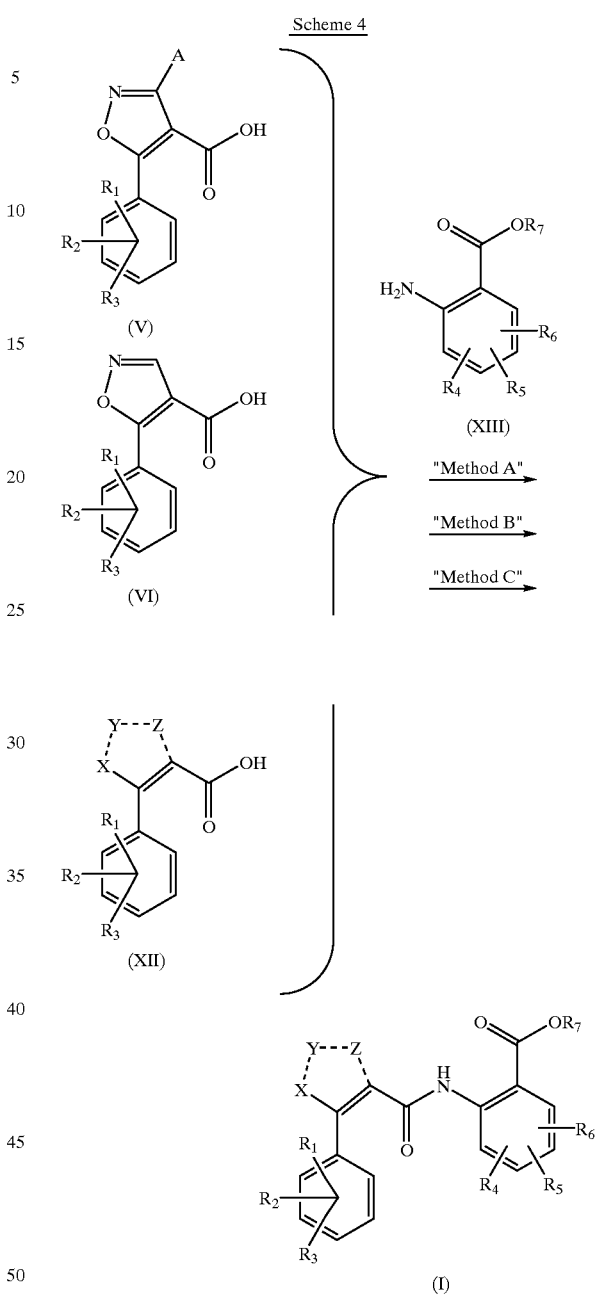

In addition to CH₂Cl₂, the reactions mentioned above may be carried out in aprotic solvents such as diethyl ether, dichloroethane, dioxane or THF at low to ambient temperatures. Where sodium hydroxide is used as a base, other inorganic bases which may also suffice are lithium hydroxide or potassium hydroxide, etc. Likewise, triethylamine may be optionally substituted with any trialkylamine.

As mentioned previously, the compounds of formula (I), and their pharmaceutically acceptable salts have been found to relax smooth muscle. They are therefore useful in the treatment of disorders associated with smooth muscle contraction, disorders involving excessive smooth muscle contraction of the urinary tract (such as incontinence), or of the gastro-intestinal tract (such as irritable bowel syndrome), asthma, and hair loss. Furthermore, the compounds of formula (I) are active as potassium channel activators which render them useful for treatment of peripheral vascular disease, congestive heart failure, stroke, anxiety, cerebral anoxia and other neurodegenerative disorders. Moreover, compounds of formula(s) (I) and (II) may also be active as chloride channel blockers, which again renders them useful for treatment of the above stated disorders.

Compounds of the present invention are characterized by their potent smooth muscle relaxing properties in vitro. The compounds of this invention exert their smooth muscle relaxatory activity via activation of potassium channels and/or blocking of chloride channels (Table 1). Comparative compound, Tranilast® was shown not to be a potent or bladder selective smooth muscle relaxant.

The present invention accordingly provides a pharmaceutical composition which comprises a compound of this invention in combination or association with pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the induction of smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLES

Example 1

2-{[2-(4-Trifluoromethyl-phenyl)-cyclopent-1-enecarbonyl]-amino}-benzoic acid

Step 1) Preparation of (O-trifluoromethylsulfonyl)-cyclopentene-2-oic acid methyl ester To a homogeneous solution of 2-carbomethoxycyclopentanone (4.00 mL, 32.2 mmol) in 1,2-dichloroethane (50 mL) at 0° C. was added triethylamine (5.84 mL, 41.9 mmol). The resultant mixture was kept at 0° C., to which was added via syringe pump over 0.5 h trifluoromethanesulfonyl anhydride (6.50 mL, 38.7 mmol). Upon completed addition, the temperature was maintained for an additional 2 h, whereupon it was subsequently diluted with EtOAc (50 mL), filtered through a short pad of $SiO_2$, eluted with 30% EtOAc-hexanes, concentrated and submitted to flash chromatography (elution with 10% EtOAc-hexanes) to yield 6.14 g (69%) of a pale yellow oil; $^1$H NMR ($CDCl_3$) δ 3.79 (s, 3 H), 2.68–2.78 (m, 4 H), 1.88–2.08 (m, 2 H).

Step 2) Preparation of 2-[4-(trifluoromethyl-phenyl)]-cyclopentenoic acid methyl ester To a mixture of the above enol triflate (1.77 g, 6.44 mmol), 4-(trifluoromethyl)-phenyltrimethylstannane [Morlein, S. M. *J. Organomet. Chem.* 1987, 319, 29–39] (1.81 g, 5.86 mmol), and anhydrous lithium chloride (745 mg, 17.6 mmol) in anhydrous dioxane was added tetrakis-(triphenylphosphine)palladium(0) (203 mg, 0.176 mmol). The resultant mixture was heated to 110° C., then stirred for 12 h. After cooling to RT, the reaction mixture was concentrated to a slurry, dissolved in ether (100 mL), filtered through a short pad of $SiO_2$, concentrated further, then submitted to flash chromatography (elution with 5% ether-petroleum ether) affording 1.155 g (73%) of a clear, colorless oil: $^1$H NMR ($CDCl_3$) δ 7.50 (ABq, 4 H), 3.63 (s, 3 H), 2.85 (m, 4 H), 2.02 (m, 2 H).

Step 3 Preparation of 2-[4-(trifluoromethyl-phenyl)]-cyclopentenoic acid

To a homogeneous solution of the above methyl ester (1.60 g, 5.92 mmol) in THF (20 mL) at RT was added 1.00 N LiOH (17.8 mL, 17.8 mmol). The resulting biphasic mixture was stirred vigorously for 16 h, whereupon all volatiles were removed by rotary evaporation. The leftover aqueous solution was washed with ether (3×100 mL), acidified to pH 2 with concentrated HCl (1.73 mL), and partitioned with ether (300 mL). The aqueous phase was then saturated with solid $NH_4Cl$, and extracted again (2×150 mL). The combined organic extracts were dried over $MgSO_4$, treated with Norite, filtered through celite, and concentrated to a solid. Trituration with ether-hexanes followed by filtration and drying in vacuo yielded 1.38 g (91%) of an off-white solid. $^1$H NMR (DMSO-$d_6$) δ 12.37 (s, 1 H), 7.65 (ABq, 4 H), 2.75–2.91 (m, 4 H), 1.92–2.02 (m, 2 H).

Step 4) Preparation of 2-{[2-(4-Trifluoromethyl-phenyl)-cyclopent-1-enecarbonyl]-amino}-benzoic acid To a heterogeneous mixture of the above carboxylic acid (500 mg, 1.95 mmol) and anhydrous DMF (4 drops) in anhydrous $CH_2Cl_2$ (3 mL) at 0° C. was added dropwise oxalyl chloride (340 μL, 3.90 mmol). The resultant mixture was warmed to RT and stirred for 2.5 h, whereupon it was concentrated to a light brown oil and purged of excess oxalyl chloride in vacuo. The neat acid chloride was then added to a homogeneous solution of anthranilic acid (535 mg, 3.90 mmol) in 2.5 N aqueous NaOH (3.12 mL, 7.80 mmol) at 5° C., resulting in the instantaneous formation of a white precipitate. The reaction mixture was then warmed to RT, whereupon it was diluted with a minimal amount of water to facilitate stirring, which was continued for an additional 1.5 h. The mixture was acidified to pH 2 by addition of concentrated HCl (0.75 mL), diluted with 2.0 N HCl, and stirred for 1.5 h. Filtration of the suspension followed by washing with water, air drying and subsequent recrystallization from MeOH afforded 118 mg (16%) of an off-white crystalline solid: mp 225.1–225.9° C.; $^1$H NMR (DMSO-$d_6$) d 13.51 (br s, 1 H), 11.28 (s, 1 H), 8.56 (dd, 1 H), 7.92 (dd, 1 H), 7.60 (ABq, 4 H), 7.12 (ddd, 1 H), 2.91 (m, 4 H), 2.03 (m, 2 H); IR (KBr) 3121, 2966, 1700, 1662, 1636, 1586, 1528, 1450, 1381, 1321, 1205, 1163, 1131, 1066, 1017, 837, 755, 694 cm$^{-1}$; MS (m/z) 375 [M$^+$].

Elemental analysis for $C_{20}H_{16}F_3NO_3$: Calc'd: C, 64.00; H, 4.30; N, 3.73. Found: C, 63.79; H, 4.08; N, 3.57.

Example 2

2-{[5-(4-Trifluoromethyl-phenyl)-oxazole-4-carbonyl]-amino}-benzoic acid

Step 1) Preparation of 5-(4-trifluoromethyl-phenyl)-oxazole-4-carboxylic acid methyl ester To a mixture of 4-trifluoromethylbenzoyl chloride (8.42 g, 40.4 mmol) and triethylamine (12.3 g, 122 mmol) in anhydrous THF was added methyl isocyanoacetate (3.60 g, 36.3 mmol). The resultant mixture was stirred at RT for 72 H whereupon all volatiles were removed via rotary evaporation, giving a residue which was partitioned between EtOAc (300 mL) and water (100 mL). The organic phase was extracted with saturated NaHCO$_3$ (100 mL), washed with brine (100 mL), dried over MgSO$_4$, treated with norite, filtered through celite, and then concentrated to afford 9.27 g (94.2%) of a brown solid which was submitted to the next reaction without further purification.

Step 2) Preparation of 5-(4-trifluoromethyl-phenyl)-oxazole-4-carboxylic acid

In a manner similar to Step 3 of Example 1 was prepared the title intermediate (83%) from commercially available 5-(4-trifluoromethyl-phenyl)-oxazole-4-carboxylic acid methyl ester.

Step 3) Preparation of 2-{[5-(4-Trifluoromethyl-phenyl)-oxazole-4-carbonyl]-amino}-benzoic acid methyl ester In a manner similar to Step 4 of Example 1 was prepared 5-(4-trifluoromethyl-phenyl)-oxazole-4-carbonyl chloride from the above carboxylic acid. The title intermediate was prepared in a manner similar to Step 1 of Example 15 from the indicated acid chloride and methyl anthranilate. Submission to flash chromatography (elution with 17% ether-hexanes) afforded a white solid (92%).

Step 4) Preparation of 2-{[5-(4-Trifluoromethyl-phenyl)-oxazole-4-carbonyl]-amino}-benzoic acid In a manner similar to Step 3 of Example 1 was prepared the title compound (45%) from the above methyl ester: mp 231–232° C.; $^1$H NMR (DMSO-d$_6$) δ 13.53 (br s, 1 H), 12.51 (s, 1 H), 8.74–8.78 (m, 2 H), 8.16 (ABq, 4 H), 8.02 (dd, 1 H), 7.62 (ddd, 1 H), 7.21 (ddd, 1 H); IR (KBr) 3449, 3245, 3080, 3022, 2647, 2559, 1669, 1607, 1585, 1519, 1466, 1451, 1410, 1327, 1261, 1151, 1126, 1060, 1017, 993, 880, 848792, 761, 662 cm$^{-1}$; MS (m/z) 376 [M$^+$].

Elemental analysis for $C_{18}H_{11}F_3N_2O_4$: Calc'd: C, 57.46; H, 2.95; N, 7.45. Found: C, 57.62; H, 3.19; N, 7.01.

Example 3

2-{[5-(4-Trifluoromethyl-phenyl)-oxazole-4-carbonyl]-amino}-benzoic acid lithium salt To a solid mixture of 2-{[5-(4-Trifluoromethyl-phenyl)-oxazole-4-carbonyl]-amino}-benzoic acid (500 mg, 1.33 mmol) and lithium hydride dust (10.6 mg, 1.33 mmol) under an atmosphere of N$_2$ was added THF (15 mL, distilled from sodium benzophenone ketyl), at RT. The heterogeneous mixture was heated at reflux for 40 h, producing a copious white precipitate, whereupon it was cooled to RT, diluted with THF (85 mL), filtered through celite, and concentrated to a white solid. The solid was then triturated with ether (40 mL, distilled from sodium benzophenone ketyl) for 72 h, producing a fine white suspension, filtered over an atmosphere of N$_2$, washed with ether (40 mL), and finally dried under high vacuum at 80° C. affording 311 mg (61%) of a white powder: mp 356.3–357.3° C. (dec); $^1$H NMR (DMSO-d$_6$) δ 15.13 (s, 1 H), 8.69 (s, 1 H), 8.63 (dd, 1 H), 8.42 (d, 1 H), 8.01 (dd, 1 H), 7.89 (d, 1 H), 7.30 (ddd, 1 H), 7.00 (ddd, 1 H); IR (KBr) 3412, 3140, 3091, 3062, 2920, 1651, 1590, 1527, 1449, 1375, 1324, 1160, 1126, 1073, 1062901, 883, 780, 759, 680 cm$^{-1}$; MS (m/z) 389 [(M+Li)$^+$].

Elemental analysis for $C_{18}H_{10}F_3N_2O_4Li$: Calc'd: C, 56.51; H, 2.62; N, 7.33. Found: C, 56.02; H, 2.44; N, 7.28.

Example 4

2-{[3-Methyl-5-(4-trifluoromethyl-phenyl)-isoxazole-4-carbonyl]-amino}-benzoic acid Step 1) Preparation of 3-[4-(trifluoromethyl-phenyl)]-prop-2-ynoic acid methyl ester To a homogeneous solution of triphenylphosphine (75.32 g, 287.1 mmol) and α,α,α-p-tolualdehyde (10.00 g, 57.43 mmol) in CH$_2$Cl$_2$ (250 mL) at 0° C. was added carbon tetrabromide (47.62 g, 143.6 mmol) as a solution in CH$_2$Cl$_2$ (50 mL). The reaction mixture was stirred at 0° C. for 5 min, then warmed to RT and stirred for an additional 4.5 h, whereupon it was poured into a vigorously stirring slurry of celite (100 g) in petroleum ether (1500 mL). The resultant mixture was stirred for 0.5 h, filtered through a pad of SiO$_2$, and concentrated to a brown oil. The oil was dissolved in petroleum ether (150 mL), treated with Norite, filtered through celite, and concentrated to afford 13.82 g (73%) of the intermediate dibromoolefin as a clear, colorless oil.

Without further purification, the dibromoolefin was dissolved in anhydrous THF (115 mL) and chilled to −78° C. To this solution was added dropwise via syringe pump over 1 h 2.5 M butyllithium (18.4 mL, 46.0 mmol). The resultant mixture was then stirred fo 0.5 h at −78° C., then treated with methyl chloroformate (5.00 mL, 64.7 mmol), followed by slow warming to RT, whereupon it was concentrated to an oily residue which was partitioned between ether (500 mL) and water (250 mL). The organic phase was washed with brine (100 mL), dried over MgSO$_4$, treated with norite, filtered, concentrated and submitted to flash chromatography (elution with 2% ether-petroleum ether) yielding 3.13 g (66%) of a white solid: $^1$H NMR (DMSO-d$_6$) δ 7.86 (ABq, 4 H), 3.79 (s, 3 H).

Step 2) Preparation of 3-methyl-5-(4-trifluoromethyl-phenyl)-isoxazole-4 carboxylic acid methyl ester To a homogeneous solution of 3-[4-(trifluoromethyl-phenyl)]-prop-2-ynoic acid methyl ester (1.00 g, 4.38 mmol) and phenyl isocyanate (857 μL, 7.89 mmol) in anhydrous benzene (2.5 mL) at RT was added dropwise a homogeneous solution of nitroethane (3.15 μL, 4.38 mmol) and distilled triethylamine (5 drops) in benzene (1.5 mL). The resultant mixture was stirred for 10 min, at which point a precipitate was formed. The reaction mixture was heated to reflux for 12 h, whereupon it was cooled to RT, diluted with ether (100 mL), and filtered to remove all solids. The filtrate was then partitioned consecutively with 1.0 N NaOH (50 mL), water (50 mL), and brine (50 mL). The organic phase was dried over Na$_2$SO$_4$, treated with Norite, concentrated, then submitted to flash chromatography (gradient elution: 10 to 15 to 20% ether-petroleum ether) affording 900 mg (72%) of a white solid: $^1$H NMR (DMSO-d$_6$) δ 8.00 (ABq, 4 H), 3.77 (s, 3 H), 2.44 (s, 3 H).

Step 3) Preparation of 3-methyl-5-(4-trifluoromethyl-phenyl)-isoxazole-4-carboxylic acid To a homogeneous solution of the above methyl ester (865. mg, 3.19 mmol) in THF (10 mL) at RT was added 1.00 N LiOH (9.57 mL, 9.57 mmol). The resulting biphasic mixture was stirred vigorously for 16 h, whereupon all volatiles were removed by rotary evaporation. The leftover aqueous solution was washed with ether (3×50 mL), acidified to pH 2 with concentrated HCl (0.93 mL), and partitioned with ether (300 mL). The aqueous phase was then saturated with solid $NH_4Cl$, and extracted again (2×150 mL). The combined organic extracts were dried over $MgSO_4$, treated with Norite, filtered through celite, and concentrated to a solid. Trituration with ether-hexanes followed by filtration and drying in vacuo to afford 735 mg (89%) of a white crystalline solid.

Step 4) Preparation of 2-{[3-Methyl-5-(4-trifluoromethyl-phenyl)-isoxazole-4-carbonyl]-amino}-benzoic acid To a heterogeneous mixture of the above carboxylic acid (1.00 g, 4.34 mmol) and anhydrous DMF (2 drops) in anhydrous $CH_2Cl_2$ (5 mL) at 0° C. was added dropwise oxalyl chloride (760 μL, 8.69 mmol). The resultant mixture was warmed to RT and stirred for 2.5 h, whereupon it was concentrated to a heterogeneous yellow mixture and purged of excess oxalyl chloride in vacuo. The acid chloride was then added to a homogeneous solution of anthranilic acid (1.19 g, 8.69 mmol) in 2.5 N aqueous NaOH (6.95 mL, 17.4 mmol) at 5° C., resulting in the instantaneous formation of a white precipitate. The reaction mixture was then warmed to RT, whereupon it was diluted with a minimal amount of water to facilitate stirring, which was continued for an additional 1.5 h. The mixture was acidified to pH 2 by addition of concentrated HCl (1.63 mL), diluted with 2.0 N HCl, and stirred for 1.5 h. Filtration of the suspension followed by washing with water, air drying and subsequent recrystallization from MeOH. The title compound which was separated from unreacted starting material by exhaustive methylation of the acid groups with (trimethylsilyl)diazomethane. The isolated 2-{[3-Methyl-5-(4-trifluoromethyl-phenyl)isoxazole-4-carbonyl]-amino}-benzoic acid methyl ester was saponified in a manner similar to Step 2 of this Example to give the title compound (60%): mp (trimethylsilyl)diazomethane. The isolated 2-{[3-Methyl-5-(4-trifluoromethyl-phenyl)-isoxazole-4-carbonyl]-amino}-benzoic acid methyl ester was saponified in a manner similar to Step 2 of this Example to give the title compound (60%): mp 204.6–205.5° C.; $^1H$ NMR (DMSO-$d_6$) δ 13.52 (br s, 1 H), 11.47 (s, 1 H), 8.42 (d, 1 H), 7.97 (ABq, 4 H), 7.93 (dd, 1 H), 7.64 (ddd, 1 H), 7.23 (ddd, 1 H) 2.47 (s, 3 H); IR (KBr) 3374, 3118, 2987, 2656, 1681, 1659, 1604, 1585, 1532, 1441, 1263, 1166, 1075, 1014, 905, 847, 762, 719, 701 $cm^{-1}$; MS (m/z) 380 $[M^+]$.

Elemental analysis for $C_{19}H_{13}F_3N_2O_4$: Calc'd: C, 58.47; H, 3.36; N, 7.18. Found: C, 58.22; H, 3.24; N, 7.02.

The smooth muscle relaxing activity of the compounds of this invention was established in accordance with standard pharmaceutically accepted test procedures with representative compounds as follows:

Sprague-Dawley rats (150–200 g) are rendered unconscious by $CO_2$ asphyxiation and then euthanized by cervical dislocation. The bladder is removed into warm (37 deg. C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; ⅖% $CO_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 μM carbachol. The carbachol is then washed out and the tissue allowed to relax to its resting level of activity. Following a further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity ($IC_{50}$ concentration) and is calculated from this concentration-response curve. The maximum percentage inhibition of contractile activity evoked by a test compound is also recorded for concentrations of test compound less than or equal to 30 μM.

The results of this study are shown in Table I.

TABLE I

Inhibition of Contractions in Isolated Rat Bladder Strips and Indication of Selectivity

| Example # | n | $IC_{50}$/μM Bladder (B) | n | $IC_{50}$/μM Aorta (A) | $IC_{50}$ (A)/ $IC_{50}$ (B) |
|---|---|---|---|---|---|
| 1 | 5 | 11.04 ± 4.04 | — | — | — |
| 2 | 2 | 17.9 ± 5.8 | — | — | — |
| 3 | 4 | 17.5 ± 12.4 | 2 | 7.35 ± 0.25 | 0.42 |
| 4 | 2 | 11.9 ± 3.95 | — | — | — |
| Tranilast ®§ | 2 | 14.4 ± 4.5 | 5 | 15.59 ± 8.96 | 1.08 |

§Tranilast is (E)-2-[3-(3,4-Dimethoxy-phenyl)-acryloylamino]-benzoic acid.
*Percent inhibition at 30 μM In addition, the ability of compounds to inhibit the hyperactivity of hypertrophied bladder (detrussor) smooth muscle in conscious female rats with hypertrophied bladders and thereby alleviate urinary incontinence in rats may be tested according to the following protocol described by Malmgrem (A Malmgrem, K. E. Andersson, C. Sjogren, P. O. Andersson, Effects of Pinacidil and Cromakalim (BRL 34915) on Bladder Function in Rats with Detrusor Instability, J. Urol. 142:1134, 1989):

Female Sprague-Dawley rats, ranging in weight from 190–210 g are used. Up to 25 animals are prepared each time. After development of bladder hypertrophy 4–8 animals are used per test.

Compounds are dissolved in PEG-200 and administered by gastric gavage or intraveneously in a volume of 5 mL/kg. For primary screening all drugs are administered at the arbitrary dose of 10 mg/kg p.o. to groups of 4 rats.

The animals are anesthetized with halothane. Through a midline incision the bladder and urethra are exposed and a ligature of 4-0 silk is tied around the proximal urethra in the presence of a stainless steel rod (1 mm diameter) to produce a partial occlusion. The rod is then removed. The abdominal region is closed using surgical staples and each rat receives 150,000 units of bicillin C-R. The animals are allowed six weeks to develop sufficient bladder hypertrophy. After six weeks, the ligature is removed under halothane anesthesia and a catheter (PE 60) with a cuff is placed in the dome of the bladder and secured with a purse string suture. The catheter is tunneled under the skin and exteriorized through an opening in the back of the neck. The abdominal incision is sutured and the free end of the catheter sealed. In order to prevent infections the rats receive an injection of bicillin C-R (150000 units/rat). Two days later the animals are used in cystometrical evaluations. The animals are placed in the metabolic cages and the catheter is attached (using a "T" connector) to a Statham pressure transducer (Model P23Db) and to a Harvard infusion pump. A plastic beaker attached to a force displacement transducer (Grass FTO3) is placed under the rat's cage to collect and record urine volume. Animals are allowed 15–30 min to rest before the saline infusion (20 mL/hr for 20 minutes) is started for the first cystometry period. Two hours after the first cystometry period, the rats are dosed with the vehicle or the test compound and one hour later a second cystometry is performed.

The following urodynamic variables are recorded:

Basal bladder pressure=the lowest bladder pressure during cystometry

Threshold pressure=bladder pressure immediately prior to micturition

Micturition volume=volume expelled

Micturition pressure=peak pressure during voiding

Spontaneous activity=mean amplitude of bladder pressure fluctuations during filling Presentation of Results The mean value of each variable is calculated before and after compound administration. For each compound the changes in the variables measured are compared to the values obtained before treatment and expressed as percent inhibition. The data are also subjected to 2-way analysis of variance to determine significant (p<0.05) changes in the variable measured.

Criteria for Activity

The most characteristic finding in this rat model is spontaneous bladder contractions which develop during filling. The compounds which inhibit spontaneous contractions by at least 50% at 10 mg/kg p.o. or i.v. (arbitrary chosen dose) are considered active.

Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating and/or chloride channel blocking compounds by administration, orally, parenterally, or by aspiration to a patient in need thereof.

What is claimed is:

1. A compound having the formula:

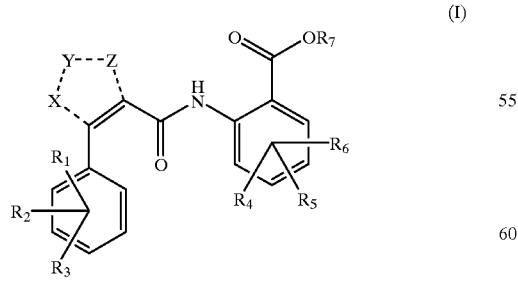

(I)

wherein:

$R_1$, $R_2$ and $R_3$ are, independently, hydrogen, nitro, cyano, $C_{1-10}$ haloalkoxy, amino, $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl and $C_{6-12}$ aryl; with the provisos: (1) that $R_1$, $R_2$ and $R_3$ may not all simultaneously be hydrogen, and (2) when $R_1$ and $R_2$ are hydrogen, $R_3$ may not be meta-$CF_3$;

$R_4$, $R_5$ and $R_6$ are, independently, hydrogen, halogen, nitro, cyano, $C_{1-10}$ carboalkoxy, $C_{1-10}$ haloalkoxy, amino $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl, $C_{1-10}$ alkyl and $C_{6-12}$ aryl;

$R_7$ is hydrogen, metal cation, acetylamido, alkoxyacetoyl or a related moiety which delivers the carboxylate in vivo; and X, Y and Z, together with the atoms to which they are attached, form a $C_{5-15}$ carbocyclic ring, oxazole, isoxazole, thiazole, isothiazole, furan, thiophene, 2H-pyrrole, pyrrole, 2-pyrroline, 3-pyrroline, imidazole, pyrazole, 1,2,3-oxadiazole or 1,2,3-triazole.

2. A compound of claim 1

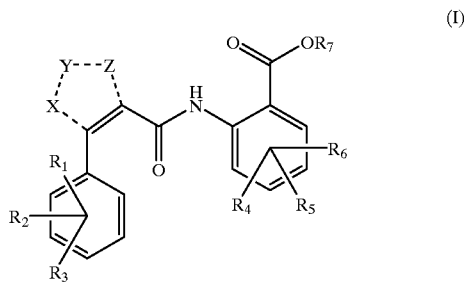

(I)

wherein:

$R_1$, $R_2$ and $R_3$ are, independently, hydrogen, nitro, cyano, perhaloalkoxy, amino, $C_{1-10}$ alkylamino, $C_{1-10}$ dialkylamino, $C_{6-12}$ arylamino, $C_{1-10}$ aralkylamino, sulfo, sulfamyl, $C_{1-10}$ alkylsulfonamido, $C_{6-12}$ arylsulfonamido, $C_{2-10}$ alkylcarboxamido, $C_{6-12}$ arylcarboxamido, $C_{2-10}$ alkanoyl, $C_{6-12}$ aryloyl, $C_{2-22}$ aralkanoyl, $C_{1-10}$ alkylsulfonyl, $C_{1-10}$ perhalosulfonyl, $C_{6-12}$ arylsulfonyl, $C_{2-22}$ aralkylsulfonyl,. $C_{1-10}$ carboxyl, $C_{1-10}$ haloalkyl, $C_{1-10}$ perhaloalkyl, aryl, haloaryl, perhaloaryl, $C_{1-10}$ aralkyl moiety; with the provisos: (1) that $R_1$, $R_2$ and $R_3$ may not all simultaneously be hydrogen, and (2) when $R_1$ and $R_2$ are hydrogen, $R_3$ may not be meta-$CF_3$;

$R_4$, $R_5$, and $R_6$, are, independent of each other, hydrogen, halogen, nitro, cyano, carboalkoxy, perhaloalkoxy, amino, $C_{1-10}$ alkylamino, $C_{1-10}$ dialkylamino, arylamino, $C_{1-10}$ aralkylamino, sulfo, sulfamyl, $C_{1-10}$ alkylsulfonamido, $C_{6-12}$ arylsulfonamido, $C_{2-10}$ alkylcarboxamido, $C_{6-12}$ arylcarboxamido, $C_{2-10}$ alkanoyl, $C_{6-12}$ aryloyl, $C_{2-22}$ aralkanoyl, $C_{1-10}$ alkylsulfonyl, $C_{1-10}$ perhalosulfonyl, $C_{6-12}$ arylsulfonyl, $C_{2-22}$ aralkylsulfonyl, $C_{1-10}$ carboxyl, $C_{1-10}$ straight chain alkyl, $C_{1-10}$ branched alkyl, $C_{3-10}$ cyclic or bicyclic alkyl, $C_{1-10}$ haloalkyl, $C_{1-10}$ perhaloalkyl, $C_{2-12}$ alkenyl (single or multiple olefinic), aryl, haloaryl, perhaloaryl, $C_{1-10}$ aralkyl;

$R_7$ is a hydrogen, an alkali metal cation, an alkaline earth metal cation, acetylamido, alkoxyacetoyl, or related moieties which deliver the carboxylate in vivo; and X, Y and Z together with the atoms to which they are attached form a $C_{5-15}$ carbocyclic ring, oxazole, isoxazole, thiazole, or isothiazole.

3. A compound of claim 1 wherein $R_7$ is selected from the group consisting of hydrogen, a metal cation, a moiety selected from:

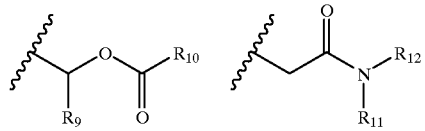

wherein:
$R_9$, $R_{10}$, $R_{11}$ and $R_{12}$, are, independent of each other, hydrogen, $C_{1-10}$ straight chain alkyl, $C_{1-10}$ branched alkyl, $C_{3-10}$ cyclic or bicyclic, aryl, or $C_{1-10}$ aralkyl; and
X, Y and Z together with the atoms to which they are attached, form a $C_{5-15}$ carbocyclic ring, oxazole, isoxazole, thiazole, or isothiazole.

4. A compound of claim 1 wherein wherein $R_7$ may be hydrogen, or a metal cation.

5. A compound of claim 1 which is 2-{[2-(4-Trifluoromethyl-phenyl)-cyclopent-1-enecarbonyl]-amino}-benzoic acid.

6. A compound of claim 1 which is 2-{[5-(4-Trifluoromethyl-phenyl)-oxazole-4-carbonyl]-amino}-benzoic acid.

7. A compound of claim 1 which is 2-{[5-(4-Trifluoromethyl-phenyl)-oxazole-4-carbonyl]-amino}-benzoic acid lithium salt.

8. A compound of claim 1 which is 2-{[3-Methyl-5-(4-trifluoromethyl-phenyl)-isoxazole-4-carbonyl]-amino}-benzoic acid.

9. A pharmaceutical composition comprising a compound having the formula:

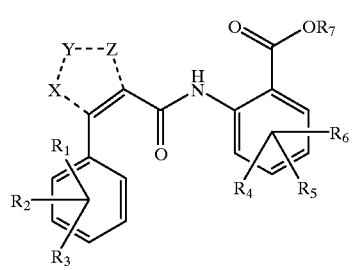

(I)

wherein:
$R_1$, $R_2$ and $R_3$ are, independently, hydrogen, nitro, cyano, $C_{1-10}$ haloalkoxy, amino, $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl and $C_{6-12}$ aryl; with the provisos: (1) that $R_1$, $R_2$ and $R_3$ may not all simultaneously be hydrogen, and (2) when $R_1$ and $R_2$ are hydrogen, $R_3$ may not be meta-$CF_3$;
$R_4$, $R_5$ and $R_6$ are, independently, hydrogen, halogen, nitro, cyano, $C_{1-10}$ carboalkoxy, $C_{1-10}$ haloalkoxy, amino $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl, $C_{1-10}$ alkyl and $C_{6-12}$ aryl;
$R_7$ is hydrogen, metal cation, acetylamido, alkoxyacetoyl or a related moiety which delivers the carboxylate in vivo; and
X, Y and Z together with the atoms to which they are attached form a $C_{5-15}$ carbocyclic ring, oxazole, isoxazole, thiazole, isothiazole, furan, thiophene, 2H-pyrrole, pyrrole, 2-pyrroline, 3-pyrroline, imidazole, pyrazole, 1,2,3-oxadiazole or 1,2,3-triazole; or pharmaceutically acceptable salt thereof; and a pharmaceutically aceptable carrier therefore.

10. A method for reducing the adverse effects of smooth muscle contractions which comprising administering, orally or parentally, to a patient in need thereof, a compound of the formula:

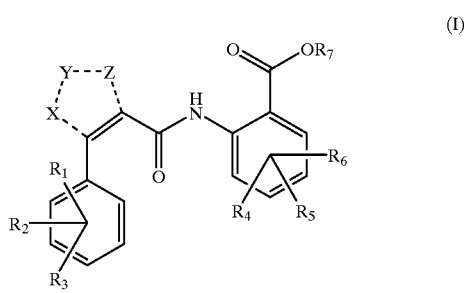

(I)

wherein:
$R_1$, $R_2$ and $R_3$ are, independently, hydrogen, nitro, cyano, $C_{1-10}$ haloalkoxy, amino, $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl and $C_{6-12}$ aryl; with the provisos: (1) that $R_1$, $R_2$ and $R_3$ may not all simultaneously be hydrogen, and (2) when $R_1$ and $R_2$ are hydrogen, $R_3$ may not be meta-$CF_3$;
$R_4$, $R_5$ and $R_6$ are, independently, hydrogen, halogen, nitro, cyano, $C_{1-10}$ carboalkoxy, $C_{1-10}$ haloalkoxy, amino $C_{1-10}$ alkylamino, sulfo, sulfamoyl, $C_{1-10}$ alkylsulfonamido, $C_{2-10}$ alkylcarboxamido $C_{2-10}$ alkanoyl, $C_{1-10}$ alkylsulfonyl, $C_{1-10}$ haloalkylsulfonyl, $C_{1-10}$ carboxyl, $C_{1-10}$ haloalkyl, $C_{1-10}$ alkyl and $C_{6-12}$ aryl;
$R_7$ is hydrogen, metal cation, acetylamido, alkoxyacetoyl or a related moiety which delivers the carboxylate in vivo; and
X, Y and Z together with the atoms to which they are attached form a $C_{5-15}$ carbocyclic ring, oxazole, isoxazole, thiazole, isothiazole, furan, thiophene, 2H-pyrrole, pyrrole, 2-pyrroline, 3-pyrroline, imidazole, pyrazole, 1,2,3-oxadiazole or 1,2,3-triazole; or pharmaceutically acceptable salts thereof.

11. The method of claim 10 wherein the smooth muscle adversely contracting causes urinary incontinence.

12. The method of claim 10 wherein the smooth muscle adversely contracting causes irritable bowel syndrome.

* * * * *